(12) United States Patent
Thoma et al.

(10) Patent No.: US 6,890,527 B2
(45) Date of Patent: May 10, 2005

(54) METHODS OF TREATMENT

(75) Inventors: John A. Thoma, Fayetteville, AR (US); Eid E. Haddad, Cary, NC (US); Craig E. Whitfill, Apex, NC (US); Alan P. Avakian, Raleigh, NC (US)

(73) Assignee: The University of Arkansas, Fayetteville, AR (US)

( * ) Notice: Subject to any disclaimer, the term of this patent is extended or adjusted under 35 U.S.C. 154(b) by 58 days.

(21) Appl. No.: 10/154,880

(22) Filed: May 24, 2002

(65) Prior Publication Data

US 2003/0044414 A1 Mar. 6, 2003

Related U.S. Application Data

(62) Division of application No. 08/938,740, filed on Sep. 26, 1997, now Pat. No. 6,440,408.
(60) Provisional application No. 60/027,084, filed on Sep. 30, 1996.

(51) Int. Cl.[7] .................. A01N 63/00; A01N 65/00; A61K 39/00; A61K 39/38; A61K 39/385
(52) U.S. Cl. .................. 424/93.1; 424/93.21; 424/93.7; 424/184.1; 424/193.1; 424/265.1; 424/269.1; 424/271.1
(58) Field of Search .................. 424/93.1, 93.21, 424/93.7, 184.1, 193.1, 265.1, 269.1, 271.1

(56) References Cited

U.S. PATENT DOCUMENTS

| | | |
|---|---|---|
| 4,795,635 A | 1/1989 | Peleg et al. |
| 4,935,007 A | 6/1990 | Bafundo et al. |
| 5,055,292 A | 10/1991 | McDonald et al. |
| 5,281,694 A | 1/1994 | Baseman et al. |
| 5,378,820 A | 1/1995 | Keeler et al. |
| 5,397,568 A | 3/1995 | Whitfill et al. |
| 5,397,569 A | 3/1995 | Whitfill et al. |
| 5,641,491 A | 6/1997 | Wilson et al. |
| 5,871,748 A | 2/1999 | Whitfill et al. |
| 5,951,976 A | 9/1999 | Segal |

FOREIGN PATENT DOCUMENTS

| | | |
|---|---|---|
| GB | 1 105 136 | 3/1968 |
| WO | WO 91 0479 | 4/1991 |
| WO | WO91/04749 | 4/1991 |
| WO | WO91/04750 | 4/1991 |
| WO | WO 9301832 | 2/1993 |
| WO | WO 9640233 | 12/1996 |

OTHER PUBLICATIONS

Bohinski, R. *Modern Concepts in Biochemistry* 5th Ed. Allyn & Bacon:38–39 (1987).
Francisco, J. et al. *Annuals of the N.Y. Academy of Science* 745:372–382 (1994).
Georgiou G. et al. *Trends in Biotechnology* 11:6–10 (1993).
Gunneriusson, E. et al. *Journal of Bacteriology* 178:1341–1346 (1996).
Hyde, R. *Immunology* 3rd Ed. Willimas & Wilkins:9–10, 46 (1995).
Karaca et al. "Effect of Temperature–Sensitive Mycoplasma Gallisepticum Vaccine Preparations and Routes of Inoculation on Resistance of White Leghorns to Challenge," *Avian Diseases*, vol. 30, No. 4, 1986, pp. 772–775.
Tizard, I. *An Introduction to Veterinary Immunology* 2nd Ed. W.B. Saunders Co.: 178–192 (1982).
Tortora, G., et al. *Microbiology, An Introduction* 3rd Ed. Benjamin/Cummings: 158 (1982).

*Primary Examiner*—Mark Navarro
(74) *Attorney, Agent, or Firm*—Myers Bigel Sibley & Sajovec, P.A.

(57) ABSTRACT

A method of producing active immunity against a bacterial or protozoal disease in a subject comprises administering to the subject a vaccine conjugate comprising a live bacteria or protozoa and a neutralizing factor bound to the live bacteria or protozoa. The neutralizing factor is selected from the group consisting of antibodies and antibody fragments. The live bacteria or protozoa is one capable of producing disease in the subject, and the antibody or antibody fragment is one capable of neutralizing the live bacteria or protozoa.

33 Claims, 3 Drawing Sheets

METHODS OF TREATMENT

RELATED APPLICATION INFORMATION

This application is a divisional of co-pending U.S. application Ser. No. 08/938,740, filed Sep. 26, 1997 (issued as U.S. Pat. No. 6,440,408 B2), which claims the benefit of U.S. Provisional Application No. 60/027,084 filed Sep. 30, 1996, the disclosures of which are incorporated by reference herein in their entireties.

FIELD OF THE INVENTION

The present invention relates to methods of producing active immunity against a bacterial or protozoal disease by administering subjects a vaccine conjugate, which conjugate is comprised of a live bacteria or protozoa and a neutralizing antibody or fragment thereof.

BACKGROUND OF THE INVENTION

Methods of producing active immunity against a viral disease by administering a vaccine conjugate, the vaccine conjugate comprised of a live virus and a viral neutralizing antibody, are described in U.S. Pat. Nos. 5,397,568 and 5,397,569 to Whitfill et al. These references are concerned with viral diseases only.

Methods of treating coccidiosis, a protozoan disease of both birds and mammals caused by various *Eimieria* species, are described in U.S. Pat. No. 4,935,007 to Baffundo et al. and U.S. Pat. No. 5,055,292 to McDonald et al. In ovo inoculation against coccidiosis is described in published PCT applications WO 96/40233 and 96/40234.

SUMMARY OF THE INVENTION

The present invention provides a method of producing active immunity against a bacterial or protozoal disease in a subject, the method comprising administering to the subject a vaccine conjugate comprised of a live bacteria or protozoa and a neutralizing factor bound to the live bacteria or protozoa. The neutralizing factor is selected from the group consisting of antibodies and antibody fragments. The antibody or antibody fragment is one capable of neutralizing the live bacteria or protozoa. The vaccine conjugate is administered in an amount effective to produce an immune response to the live bacteria or protozoa in the subject.

Another aspect of the present invention is a vaccine preparation useful for producing active immunity against a bacterial or protozoal disease in a subject. The vaccine preparation is a pharmaceutically acceptable formulation which comprises a vaccine conjugate. The vaccine conjugate comprises a live bacteria or protozoa and a neutralizing factor bound to the live bacteria or protozoa. The neutralizing factor is selected from the group consisting of antibodies and antibody fragments. The antibody or antibody fragment is capable of neutralizing the live bacteria or protozoa. The vaccine conjugate is included in the pharmaceutically acceptable formulation in an amount effective to produce an immune response to the live bacteria or protozoa in the subject.

Another aspect of the present invention is an article of manufacture comprising a closed, pathogen-impermeable, container and a sterile vaccine formulation as described above enclosed within the container.

DETAILED DESCRIPTION OF THE INVENTION

Figure 1:
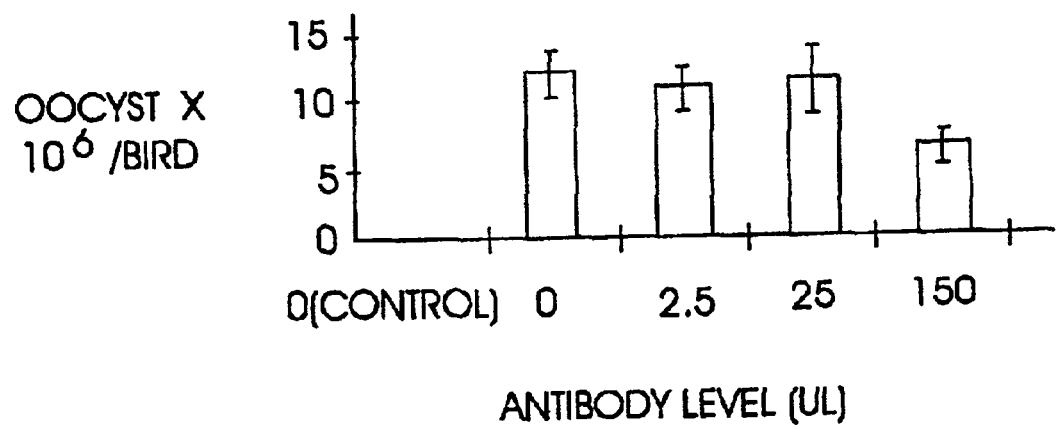
FIG. 1 graphs the oocyst output in avians vaccinated with a vaccine conjugate comprising 500 *E. acervulina* oocysts complexed with either 2.5, 25 or 150 µl of polyclonal antibody, compared to a non-vaccinated control (cntrl) and a control vaccinated with oocysts but without antibody. Oocyst output is used as a measure of infectivity.

The present invention provides a vaccine preparation comprising a live organism (bacteria or protozoa) complexed with neutralizing antibodies specific to that organism. The amount of complexed neutralizing antibodies is such that the organism remains capable of inducing an active immune response, while at the same time providing some degree of protection against the deleterious effects of the pathogen. While applicants do not wish to be held to any single theory, it is currently believed that the present vaccine complex results in some form of delayed release of the pathogenic organism.

The present vaccine complex is thought to delay or initially protect the vaccinated subject from the pathogenic effects of the vaccine organism. However, this delay or initial protection is only temporary (in contrast to what would be expected using a dead or inactivated vaccine organism). The vaccine organism in the complex does ultimately infect the subject, inducing an active immunity. The degree of delay will be dependent on the amount of antibody used, the particular vaccine organism, and the subject to be vaccinated. Such a delay in infection is important when vaccinating young subjects, particularly when large numbers of subjects are to be vaccinated. For example, it is easier and more cost-efficient to vaccinate chicks in ovo compared to vaccinating newly hatched chicks.

In a preferred embodiment of the present invention, the neutralizing factor is provided in an amount which delays the appearance of pathological changes associated with infection of the subject by the live vaccine organism. The "delay" is comparative; the pathological changes are delayed in comparison to those which would occur if the live vaccine organism were administered without complexed neutralizing factor.

Use of the present vaccine conjugates are safer than the use of the unconjugated organism yet are capable of inducing a protective active immune response. The term "safe" is used herein to indicate that the benefits of vaccination outweigh any harm in the majority of individuals vaccinated.

Antibodies used in practicing the present invention are bacterial or protozoal neutralizing antibodies. Bacterial or protozoal neutralizing antibodies are those which combat the infectivity of a bacteria or protozoa in vivo if the bacteria or protozoa and the antibodies are allowed to react together for a sufficient time. The source of the bacterial or protozoal neutralizing antibody is not critical. They may originate from any animal, including birds (e.g., chicken, turkey) and mammals (e.g., rat, rabbit, goat, horse). The bacterial or protozoal neutralizing antibodies may be polyclonal or monoclonal in origin. See. e.g. D. Yelton and M. Scharff, 68 *American Scientist* 510 (1980). The antibodies may be chimeric. See, e.g., M. Walker et al., 26 *Molecular Immunology* 403 (1989).

Bacterial or protozoal neutralizing antibodies used in practicing the present invention may be immunoglobulins of any isotype, including IgM, IgG, IgA, IgD, and IgE immunoglobulins. IgG and IgM are more preferred, and IgG immunoglobulins (e.g., IgG1, IgG2, IgG3, IgG4) are most preferred.

Antibody fragments used in practicing the present invention are fragments of bacterial or protozoal neutralizing antibodies which retain the variable region binding site thereof. Exemplary are F(ab')$_2$ fragments, F(ab') fragments, and Fab fragments. See generally Immunology: Basic Processes, 95–97 (J. Bellanti Ed. 2d ed. 1985).

Antibodies or antibody fragments used in practicing the present invention may have additional elements joined thereto. For example, a microsphere or microparticle may be joined to the antibody or antibody fragment, as described in U.S. Pat. No. 4,493,825 to Platt, the disclosure of which is incorporated herein by reference.

The present invention is particularly advantageously employed with bacteria or protozoa which would be pathogenic (i.e., capable of causing disease) in the subject being treated if not for their conjugation to the neutralizing factor. The pathogenicity of the bacteria or protozoa may be inherent in the bacteria or protozoa itself or due to the susceptibility of the subject to be treated (e.g., birds in ovo). In general, many pathogenic bacteria or protozoa have the positive effect of evoking active immunity in subjects infected therewith, and many attenuated vaccine strains of bacteria or protozoa have the capability of causing at least some disease in subjects. Hence, the term "pathogenic," as used to describe bacteria or protozoa herein, means that the harm caused to subjects by administration of the bacteria or protozoa outweighs any benefit which would result therefrom. An "active" or "live" organism refers to one which is not killed. A "vaccine organism" refers to one which is used for the induction of protective immune response, even though negative side effects may occur (in such cases the benefit of the active immunity outweighs any negative side effects). It is preferred that the bacteria or protozoa be a live organism one capable of producing an active immune response thereto in the subject being treated.

The vaccine conjugate is included in the vaccine formulations in an amount per unit dose sufficient to evoke an active immune response to the bacteria or protozoa in the subject to be treated. The term "immune response," as used herein, means any level of protection from subsequent exposure to the bacteria or protozoa which is of some benefit in a population of subjects, whether in the form of decreased mortality, decreased lesion scores, improved feed conversion ratios, or the reduction of any other detrimental effect of the disease, regardless of whether the protection is partial or complete.

With respect to the degree of protection provided by the neutralizing factor, the quantity of the neutralizing factor administered in combination with the bacteria or protozoa in the vaccine need not be sufficient to provide complete protection from the bacteria or protozoa, as long as the detrimental response produced by the bacteria or protozoa is reduced to a level at which the benefits of the immune response produced outweigh any harm resulting from the infection.

The term "subjects," as used herein, is intended to include, among other things, both mammals and birds. Exemplary mammals include mice, rats, pigs, rabbits, sheep, ferrets, dogs, cats, cows, horses and primates, including man. The term "bird" is intended to include males or females of any avian species, but is primarily intended to encompass poultry which are commercially raised for eggs or meat. Accordingly, the term "bird" is particularly intended to encompass hens, cocks and drakes of chickens, turkeys, ducks, geese, quail and pheasant.

Bacteria that may be used in carrying out the present invention include, but are not limited to, *Actinobacillosis lignieresi, Actinomyces bovis, Aerobacter aerogenes, Anaplasma marginale, Bacillus anthracis, Borrelia anserina; Brucella canis, Clostridium chauvoei, C. hemolyticium C. novyi, C perfringens, C. septicum, C. tetani, Corynebacterium equi, C. pyogenes, C. renale, Cowdria ruminantium, Dermatophilus congolensis, Erysipelothrix insidiosa, Escherichia coli, Fusiformis necrophorus, Haemobartonella canis, Hemophilus* spp. *H. suis, Leptospira* spp., *Moraxella bovis, Mycoplasma* spp. *M hyopneumoniae, Nanophyetus salmincola, Pasteurella anatipestifer, P. hemolytica, P. multocida, Salmonella abortus-ovis, Shigella equirulis, Staphylococcus aureus, S. hyicus. S. hyos, Streptococcus agalactiae, S. dysgalactiae, S. equi, S. uberis,* and *Vibrio fetus* (for the corresponding diseases, see Veterinary Pharmacology and Therapeutics 5th Edition, pg 746 Table 50.2 (N. Booth and L. McDonald Eds., 1982)(Iowa State University Press); and *Corynebacterium diptheriae, Mycobacterium bovis, M. leprae, M tuberculosis, Nocardia asteroides, Bacillus anthracis, Clostridium botulinum, C. difficile, C. perfringens, C. tetani, Staphylococcus aureus, Streptococcus pneumoniae, S. pyogenes, Bordetella pertusiss, Psudomonas aeruginos, Campylobacter jejuni, Brucella* spp., *Francisella tularenssis, Legionella pneumophila, Chlamydia psittaci. C. trachomatis, Escherichia coli, Klebsiella pneumoniae, Salmonella typhi, S. typhimurium, Yersinia enterocolitica, Y pestis, Vibrio cholerae, Haemophilus influenza, Mycoplasma pneumoniae, Neiseseria gonorrhoeae, N meninigitidis, Coxiella burneti, Rickettsia mooseria, R. prowazekii, R. rickettsii, R. tsutsugamushi, Borrelia* spp., *Leptospira interrogans, Treponema pallidum,* and *Listeria monocytogenes* (for the corresponding diseases see R. Stanier et al., The Microbial World, pg. 637–38 Table 32.3 (5th Edition 1986).

Protozoa that may be used in carrying out the present invention include, but are not limited to, the coccidiosis-causing *Eimeria* species (*E. tenella, E. necatrix, E. brunetti, E. acervulina, E. mivati,* and *E. maxima*), *Anaplasma marginale, Giardia* species (e.g., *Giardia lamblia*), *Babesia* species (e.g., *B. canis, B. gibsoni, B. equi, B. caballi, B. bigemina, B. argentina, B. divergens,* and *B. bovis*) *Trichomonas foetus, Entamoeba histolytica,* and *Balantidium coli; Plasmodium* species (e.g., *P. falciparum, P. malariae, P. vivax,* and *P. ovale*), *Leishmania* species (e.g., *L. donovani, L. braziliensis, L. tropica,* and *L. mexicana*), *Trypanosoma* species e.g., *T brucei* and *T. cruzi*), *Entamoeba histolytica, Trichomonas vaginalis, Toxoplasmosa gondii,* and *Pneumocystis carinii*. As used herein, an "avian protozoan" is one known to infect avians.

The organisms may be administered in any suitable form, including spores or cysts thereof For example, infective coccidial organisms may be administered in the form of sporulated oocysts, sporozoites, and sporocysts.

The exact number of the organisms to be administered in the form of a conjugate is not critical except that the number must be effective to engender an immunological response by the animal. In general, depending on the organism administered, the site and manner of administration, the age and condition of the subject, etc., the number of the organisms will range from 1, 10, or 100 organisms up to 1,000, 10,000, 100,000 or 1 million organisms. Where the organisms are administered as a conjugate to birds in ovo (within eggs), the dosage may be from 50, 100, or 500 up to 2,000, 10,000, 20,000, 30,000, 50,000 or 100,000 organisms or more.

Subjects may be administered vaccines of the present invention by any suitable means. Exemplary are by oral administration, by intramuscular injection, by subcutaneous injection, by intravenous injection, by intraperitoneal injection, by eye drop or by nasal spray. When the subject to be treated is a bird, the bird may be a hatched bird, including a newly hatched (i.e., about the first three days after hatch), adolescent, and adult birds. Birds may be administered the vaccine in ovo, as described in U.S. Pat. No. 4,458,630 to Sharma (the disclosure of this and all other patent references cited herein is to be incorporated herein by reference).

The in ovo administration of the vaccine involves the administration of the vaccine to eggs. Eggs administered the vaccine of the present invention are fertile eggs which are preferably in the fourth quarter of incubation. Chicken eggs are treated on about the fifteenth to nineteenth day of incubation, and are most preferably treated on about the eighteenth day of incubation (the eighteenth day of embryonic development). Turkey eggs are preferably treated on about the twenty-first to twenty-sixth day of incubation, and are most preferably treated on about the twenty-fifth day of incubation.

Eggs may be administered the vaccine of the invention by any means which transports the compound through the shell. The preferred method of administration is, however, by injection. The site of injection is preferably within either the region defined by the amnion, including the amniotic fluid and the embryo itself, in the yolk sac, or in the air cell. Most preferably, injection is made into the region defined by the amnion. By the beginning of the fourth quarter of incubation, the amnion is sufficiently enlarged that penetration thereof is assured nearly all of the time when the injection is made from the center of the large end of the egg along the longitudinal axis.

The mechanism of egg injection is not critical, but it is preferred that the method not unduly damage the tissues and organs of the embryo or the extraembryonic membranes surrounding it so that the treatment will not decrease hatch rate. A hypodermic syringe fitted with a needle of about 18 to 22 gauge is suitable for the purpose. To inject into the air cell, the needle need only be inserted into the egg by about two millimeters. A one inch needle, when fully inserted from the center of the large end of the egg, will penetrate the shell, the outer and inner shell membranes enclosing the air cell, and the amnion. Depending on the precise stage of development and position of the embryo, a needle of this length will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

It is envisioned that a high speed automated egg injection system for avian embryos will be particularly suitable for practicing the present invention. Numerous such devices are available, exemplary being those disclosed in U.S. Pat. No. 4,681,063 to Hebrank and U.S. Pat. Nos. 4,040,388, 4,469, 047, and 4,593,646 to Miller. All such devices, as adapted for practicing the present invention, comprise an injector containing the vaccine described herein, with the injector positioned to inject an egg carried by the apparatus with the vaccine. Other features of the apparatus are discussed above. In addition, if desired, a sealing apparatus operatively associated with the injection apparatus may be provided for sealing the hole in the egg after injection thereof.

Preferred egg injection apparatus for practicing the present invention is disclosed in U.S. Pat. Nos. 4,681,063 and 4,903,635 to Hebrank, the disclosures of which are incorporated herein by reference. This device comprises an injection apparatus for delivering fluid substances into a plurality of eggs and suction apparatus which simultaneously engages and lifts a plurality of individual eggs from their upwardly facing portions and cooperates with the injection means for injecting the eggs while the eggs are engaged by the suction apparatus. The features of this apparatus may be combined with the features of the apparatus described above for practicing the present invention. Preferred subjects for carrying out the present invention are birds.

The method of the present invention is preferably carried out on birds in ovo.

A vaccine conjugate of the present invention is made by mixing the neutralizing factor with a live bacteria or protozoa in a pharmaceutically acceptable carrier for a time sufficient to form a live bacteria or protozoa-neutralizing factor conjugate (for example, by combining the neutralizing factor and bacteria or protozoa in a common liquid carrier prior to administration to a subject, until a conjugate is formed). This can advantageously be carried out by simply adding hyperimmune sera containing neutralizing antibodies to an aqueous solution containing the live bacteria or protozoa. Vaccine formulations of the present invention preferably comprise the vaccine conjugate in lyophilized form or the vaccine conjugate in a pharmaceutically acceptable carrier. Pharmaceutically acceptable carriers are preferably liquid, particularly aqueous, carriers. For the purpose of preparing such vaccine formulations, the neutralizing factor and bacteria or protozoa may be mixed in sodium phosphate-buffered saline (pH 7.4), conventional media such as MEM, or bacterila growth medium. The vaccine formulation may be stored in a sterile glass container sealed with a rubber stopper through which liquids may be injected and formulation withdrawn by syringe.

The vaccine conjugate or complex of the present invention is a complex or conjugate of antibodies and live vaccine organisms; the bond between antibody and vaccine organism is a releasable bond and is not a covalent bond. The amount of neutralizing antibodies suitable for use with a given vaccine organism and a given subject can be readily determined using techniques available in the art. Use of too little antibody will result in undesirably early or severe pathogenic effects caused by the vaccine organism; use of too much antibody may inactivate the vaccine organism completely or render it incapable of inducing a protective immune response.

Vaccine formulations of the present invention may optionally contain one or more adjuvants. Any suitable adjuvant can be used, including chemical and polypeptide immunostimulants which enhance the immune system's response to antigens. Preferably, adjuvants such as aluminum hydroxide, aluminum phosphate, plant and animal oils, and the like are administered with the vaccine conjugate in an amount sufficient to enhance the immune response of the subject to the vaccine conjugate. The amount of adjuvant added to the vaccine conjugate will vary depending on the nature of the adjuvant, generally ranging from about 0.1 to about 100 times the weight of the bacteria or protozoa, preferably from about 1 to about 10 times the weight of the bacteria or protozoa.

The vaccine formulations of the present invention may optionally contain one or more stabilizer. Any suitable stabilizer can be used, including carbohydrates such as sorbitol, manitol, starch, sucrose, dextrin, or glucose; proteins such as albumin or casein; and buffers such as alkaline metal phosphate and the like. The use of a stabilizer is particularly advantageous when the vaccine formulation is a lyophilized formulation.

The present invention is explained in greater detail in the following non-limiting Examples.

EXAMPLE 1

Bacterial Species

The bacterium *Pasteurella multocida* causes an acute highly contagious disease in many avian species. The disease, Fowl cholera, often occurs as a septicemic disease resulting in high morbidity and mortality. There are several live vaccines for Fowl cholera that can be administered to both chickens and turkeys.

A strain of *P. multocida* is complexed in vitro with antibodies specific to *P. multocida* to form bacterium-antibody complexes. Different ratios of bacterium to antibody are tested to determine a ratio that does not completely inactivate the bacterium, and still allows an active immune response to occur. These complexes are used as a vaccine in either chickens or turkeys. The responses of the vaccinate are followed and compared to the responses of birds vaccinated with the same dose of *P. multocida* vaccine not complexed with antibody. Lesions following vaccination, antibody response over time and general bird healty are monitored throughout the trial.

Other bacteria are also tested in a similar manner. These bacteria include, but are not limited to, *Mycoplasma gallisepticum* in chickens or turkeys, *Bordetella avium* in turkeys, *Salmonella* species in chickens or turkeys, and *Salmonella* and *Listeria* species in rodents.

Vaccine conjugates are administered to birds either in ovo as described above or after hatch.

EXAMPLE 2

Protozoal Species

The protozoan *Eimeria acervulina* (specifically, sporocysts and/or oocysts thereof) is complexed in vitro to antibodies specific to *Eimeria acervulina* to form protozoan-antibody complexes. These complexes are used as vaccines in chickens. The responses of the protozoan-antibody complex vaccinates are followed and compared to the responses of birds vaccinated with the same dose of *E acervulina* not complexed with antibody. Different ratios of protozoan to antibody are tested to deterimine a ratio that does not completely inactivate the protozoan, and still allows an active immune response to occur. Oocyst output in vaccinates feces, intestinal absorptive ability (assessed by cartenoid uptake) and body weight are determined post vaccination. At 10–21 days post vaccination birds in each vaccinated group are given a virulent challenge with *E. acervulina* Oocyst output in vaccinates feces, body weight gain during the challenge period and intestinal absorptive ability (assessed by cartenoid uptake) are determined for vaccinates and non-vaccinated controls.

Other *Eimeria* species are also tested in chickens, turkeys or rodents, as well as *Cryptosporidium* species in chickens or turkeys and *Histomonas meleagridis* in chickens or turkeys.

Vaccine conjugates are administered to birds either in ovo as described above or after hatch.

EXAMPLE 3

*Eimeria* Oocyst Output Following Vaccination

Chickens were vaccinated and studied to determine the effects of complexing an *E. acervulina* oocyst vaccine with antibody.

Four vaccination strategies were studied. Treatment groups were vaccinated (by oral gavage) with 500 *E. acervulina* sporulated oocysts complexed with either 0, 2.5, 25 or 150 units of polyclonal antibody specific for *E. acervulina*. Each treatment was provided to three groups of five Leghorn chickens (15 birds total in each treatment group; 60 treatment birds overall). A control group of fifteen birds (5 birds in three repetitions) received no oocysts and no antibody, but were treated with oral gavage of 0.1 ml PBS administered on the day of hatch and were subsequently challenged.

Units of antibody is defined on a volumetric basis, where 1 μl=1 unit. An ELISA assay has been used to determine the "titer units" of the antibody preparation used in the present example; however, this assay has not been validated. By the ELISA assay, the *E. acervulina* antibody preparation had a titer of 90,782 units/ml. The doses used herein provide relative comparisons; the appropriate amount of antibody to be complexed with a given organism will depend on the organism, the antibody preparation, and the intended subject. One skilled in the art, using techniques known in the art, would be able to determine appropriate organism:antibody ratios for a given usage.

The oocysts and antibodies were mixed together in PBS for a minimum of one hour prior to vaccination at room temperature. Vaccine complex was then stored at 4 C until administration. Chickens were vaccinated on the day of hatch.

Oocyst output following vaccination was determined by collecting feces on days 4 to 8 post vaccination, and counting oocyst in the feces. The mean and standard deviation of oocyst output was determined for each group. As shown in Table 1, use of 150 μl of antibodies complexed with 500 oocysts significantly reduced oocyst output.

TABLE 1

Infectivity-Oocyst Output per Bird

| Vaccination Treatment | Average Oocysts/Bird ($x\ 10^6$) |
|---|---|
| None | |
| Mean | 0.00 |
| Standard Deviation | 0.00 |
| N | 3[2] |
| 0 μl Abs + oocysts | |
| | (a)[1] |
| Mean | 11.65 |
| Standard Deviation | 2.91 |
| N | 3[2] |
| 2.5 μl Abs + oocysts | |
| | (a)[1] |
| Mean | 10.18 |
| Standard Deviation | 2.54 |
| N | 3[2] |

TABLE 1-continued Infectivity-Oocyst Output per Bird

| Vaccination Treatment | Average Oocysts/Bird (x $10^6$) |
|---|---|
| 25 µl Abs + oocysts | |
| | (a)[1] |
| Mean | 10.61 |
| Standard Deviation | 4.28 |
| N | 3[2] |
| 150 µl Abs + oocysts | |
| | (b)[1] |
| Mean | 5.40 |
| Standard Deviation | 1.94 |
| N | 3[2] |

[1] a, b: differed at the 0.15 level by LSD test. Significance set at the 0.20 level due to the small sample size. Controls were not included in the statistical model.
[2] N = Three groups of five birds in each group.

EXAMPLE 4

*Eimeria* Oocyst Output Following Challenge

Birds in the treatment groups described in Example 1 were then challenged on Day 13 posthatch with 250 oocysts of *E. acervulina* in PBS administered by oral gavage. Feces was collected on days four to eight post-challenge, and average oocyst output was determined as a percentage of the oocyst output of the control group (the statistical model included the control group). Results are provided in Table 2. Greater output of oocysts following challenge indicates less protection against the pathogen challenge.

TABLE 2

Protection after Challenge

| Vaccination Treatment | Average Oocyst Output per Bird; Post-challenge (x $10^6$) | Average Oocysts (% of control)[2] |
|---|---|---|
| Control[2] | | |
| | A[1] | A[1] |
| Mean | 23.08 | 100.00 |
| Standard Deviation | 1.67 | 7.22 |
| N | 3 | 3 |
| 0 µl Abs + oocysts | | |
| | C[1] | C[1] |
| Mean | 5.20 | 22.54 |
| Standard Deviation | 0.72 | 3.13 |
| N | 3 | 3 |
| 2.5 µl Abs + oocysts | | |
| | B[1] | C[1] |
| Mean | 8.72 | 37.76 |
| Standard Deviation | 2.45 | 10.60 |
| N | 3 | 3 |
| 25 µl Abs + oocysts | | |
| | B[1] | B[1] |
| Mean | 9.76 | 42.29 |
| Standard Deviation | 1.78 | 7.70 |
| N | 3 | 3 |

TABLE 2-continued

Protection after Challenge

| Vaccination Treatment | Average Oocyst Output per Bird; Post-challenge (x $10^6$) | Average Oocysts (% of control)[2] |
|---|---|---|
| 150 µl Abs + oocysts | | |
| | B[1] | B[1] |
| Mean | 10.49 | 45.47 |
| Standard Deviation | 2.33 | 10.10 |
| N | 3 | 3 |

[1] A, B, C: differed at the .05 level by SNK test.
[2] Control = non-vaccinated, challenged birds.

EXAMPLE 5

Protection Following Challenge

Data provided in Table 2 was re-analyzed without including the control group data in the statistical model. Results are provided in Table 3.

TABLE 3

| Vaccination Treatment | Average Oocysts Post-challenge (x $10^6$) | Average Oocysts (% of control) |
|---|---|---|
| Control[2] | | |
| Mean | 23.08 | 100.00 |
| Standard Deviation | 1.67 | 7.22 |
| N | 3 | 3 |
| 0 µl Abs + oocysts | | |
| | B[1] | B[1] |
| Mean | 5.20 | 22.54 |
| Standard Deviation | 0.72 | 3.13 |
| N | 3 | 3 |
| 2.5 µl Abs + oocysts | | |
| | AB[1] | AB[1] |
| Mean | 8.72 | 37.76 |
| Standard Deviation | 2.45 | 10.60 |
| N | 3 | 3 |
| 25 µl Abs + oocysts | | |
| | A[1] | A[1] |
| Mean | 9.76 | 42.29 |
| Standard Deviation | 1.78 | 7.70 |
| N | 3 | 3 |
| 150 µl Abs + oocysts | | |
| | A[1] | A[1] |
| Mean | 10.49 | 45.47 |
| Standard Deviation | 2.33 | 10.10 |
| N | 3 | 3 |

[1] A, B, C: differed at the .05 level by SNK test.
[2] Control = non-vaccinated, challenged birds.

The results provided in Examples 1–3 indicate that use of 150 µl antibody in conjunction with the vaccination dose of 500 *E acervulina* oocysts resulted in either a lessening of the pathogenic effects of the vaccination (compared to use of same vaccination with lesser amounts of antibody, or no antibody; indicated by decreased oocysts output after vaccination), or possibly a delay in the pathogenic effects of the vaccination dose. As shown in Table 1, the use of 150 µl of antibody complexed to the vaccine oocysts resulted in a lower infectivity level than vaccination without antibodies or the use of lesser amounts of antibodies ($p \leq 0.15$).

As shown in Table 2, birds vaccinated with antibody-oocyst vaccine had reduced oocyst output after challenge with 250 E. acervulina oocysts, compared to unvaccinated birds. These results indicate that the antibody-oocyst vaccine preparation is effective in inducing a protective immune response against the challenging pathogen. Protection was highest in the treatment group vaccinated with oocysts but without any antibody, with a significance level of 0.05. As shown in Table 3, among birds treated with antibody-oocyst vaccine, the highest protection is again seen in the group treated with oocyst but no antibody.

The above results indicate that use of a vaccine complex of antibody and oocyst resulted in either a lessening of the pathogenic effects of the vaccine oocysts, or a delay in the pathogenic effects of the vaccine oocysts, while still engendering a protective immune response. Either effect would be expected to increase the safety of a vaccine, either by allowing administration of the vaccine to subjects who are more susceptible to the pathogenic effects of the vaccine organism, or to subjects at a younger age (such as to avians in ovo).

The foregoing are illustrative of the present invention, and are not to be taken as limiting thereof. The invention is defined by the following claims, with equivalents of the claims to be included therein.

EXAMPLE 6

Use of Antibody-Oocyst (*Eimeria acervulina*) Vaccine Conjugate in Low-Dose Challenge Model This study tested a 500 *Eimeria acervulina* oocyst vaccine complexed with varying amounts of antibody (2.5 to 150 $\mu$l). Treatments were compared to a non-vaccinated control, and a control vaccinated without antibodies. All treatments were administered on the day of hatch. Oocyst output after vaccination on Days 4–8 was measured for all treatments. Oocyst output was also measured after a Day 13 low dose challenge.

Materials and Methods: Hyvac SPF leghorns were used to rule out any effect of maternal antibodies. Polyclonal antibody was produced from chickens immunized with *E. acervulina* oocysts. Two antibody preparations were combined to create an *E. acervulina* antibody with a final titer of 90,782. Treatment groups and experimental design are shown in Table 4.

TABLE 4

| Treatment | Oocyst Dose | Antibody ($\mu$l) | # of Birds/Rep | # Reps | Total # of Birds |
|---|---|---|---|---|---|
| 1 (A, B, C) | 0 | 0 | 5 | 3 | 15 |
| 2 (A, B, C) | 500 | 0 | 5 | 3 | 15 |
| 3 (A, B, C) | 500 | 2.5 | 5 | 3 | 15 |
| 4 (A, B, C) | 500 | 25 | 5 | 3 | 15 |
| 5 (A, B, C) | 500 | 150 | 5 | 3 | 15 |

The vaccine complex was produced by mixing oocysts (USDA #12 Lot 28-131-36) with antibody in the appropriate volume. The complex was incubated at ambient temperature for one hour before administration. Birds were gavaged on Day of Hatch with a 200 $\mu$l dose of the respective treatment. Fecal material was collected form Day 4 to Day 8. Fecal samples were processed and counted using McMaster's chambers to determine oocyst output per bird.

Birds were moved to a brooder unit and challenged on Day 13 post-hatch with a low dose challenge (250 *E. acervulina* oocysts). Feces was collected Days 4–8 post challenge and enumerated as described above.

The vaccinated control showed $\cong 12\times10^6$ oocyst output per bird. The 2.5 $\mu$l and 25 $\mu$l antibody treatments showed similar results, however, the 150 $\mu$l antibody treatment may have had an inhibitory effect on oocyst output, having only 46% of the output compared to the control. See FIG. 1.

Figure 3:
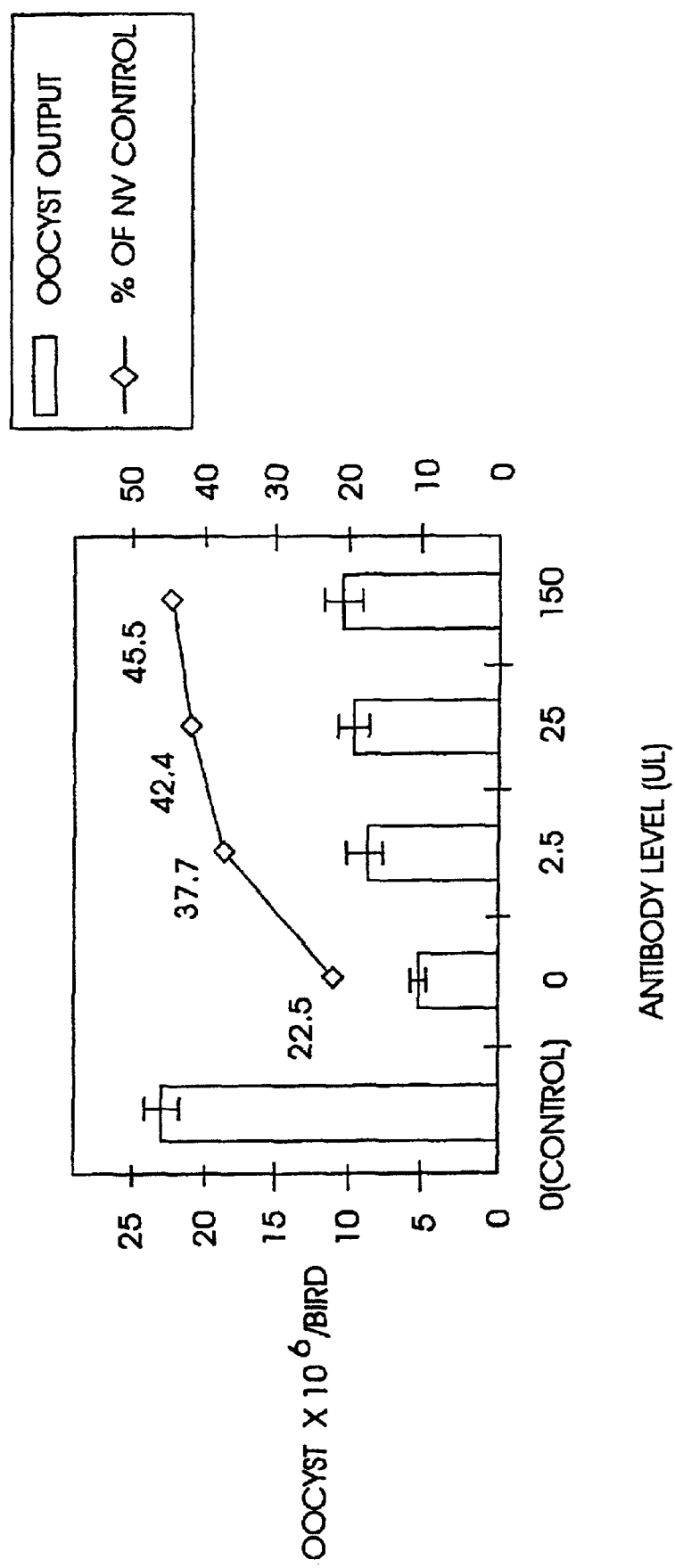
FIG. 3 graphs oocyst output after vaccination and low-dose *E. acervulina* challenge. Vaccination used a vaccine conjugate comprising 500 *E. acervulina* oocysts complexed with either 2.5, 25 or 150 µl of polyclonal antibody; controls were a non-vaccinated control (cntrl) and a control vaccinated with oocysts but without antibody (0).

After a low dose challenge, similar results were seen in all the antibody vaccinated treatment groups. FIG. 3. The three antibody treatment groups averaged approximately 40% output of control. The vaccinated control exhibited an output of only 23% of control.

EXAMPLE 7

Use of Antibody-Oocyst (*Eimeria acervulina*) Vaccine Conjugate in High-Dose Challenge Model Two antibody-oocyst vaccine conjugate formulations were tested in a high-dose challenge model. Infectivity was measured by oocyst output and response to challenge was measured by weight gain and lesion scores. The vaccine conjugates consisted of 500 *E. acervulina* oocysts complexed with either 25 or 150 $\mu$l of antibody (as described in Example 6); see Table 5. The same bird strain, antibody, and oocyst lot was used as in Example 6 above.

TABLE 5

| Treatment # | Oocyst Dose | Antibody ($\mu$l) | # of Birds/Rep | # Reps | Total # Of Birds |
|---|---|---|---|---|---|
| 1 (A, B, C) | 0 | 0 | 10 | 3 | 30 |
| 2 (A, B, C) | 500 | 0 | 10 | 3 | 30 |
| 3 (A, B, C) | 500 | 25 | 10 | 3 | 30 |
| 4 (A, B, C) | 500 | 150 | 10 | 3 | 30 |

Vaccines were prepared as described above and administered on Day 0 post-hatch in 200 $\mu$l volume. Fecal material was collected from Day 4–8 and enumerated.

Post-challenge parameters measured in the present experiment differed from Example 6. A high dose challenge was administered to all treatment groups on Day 13 and weights of each individual bird were recorded. After eight days (Day 21) the birds were weighed and the lesions scored.

Figure 2:
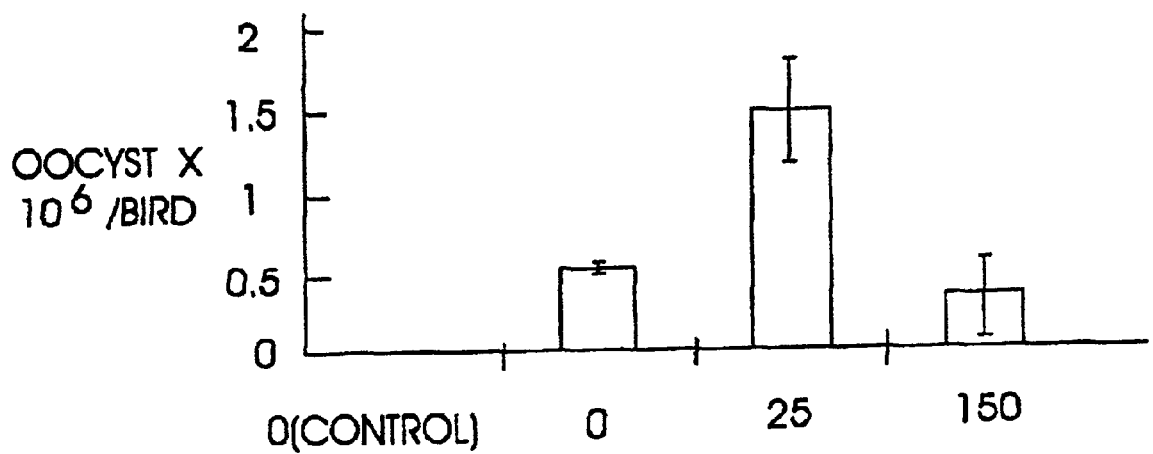
FIG. 2 graphs the oocyst output in avians vaccinated with a vaccine conjugate comprising 500 *E. acervulina* oocysts complexed with either 25 or 150 µl of polyclonal antibody, compared to a non-vaccinated control (cntrl) and a control vaccinated with oocysts but without antibody. Oocyst output is used as a measure of infectivity.

Oocyst output was lower in this experiment for the vaccinated control, as well as for the two antibody treatments, compared to Example 6; the vaccinated control (no antibody) showed a 20-fold decrease in oocyst output (see FIG. 2). The cause of this reduction is not clear.

Figure 4:
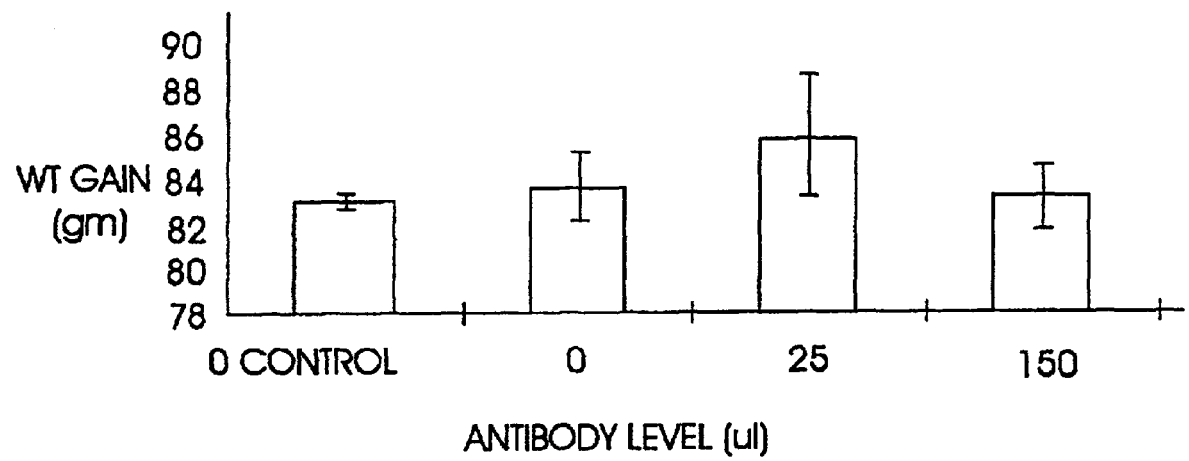
FIG. 4 graphs weight gain (in grams) in birds after vaccination and a high-dose *E. acervulina* challenge. Vaccination used a vaccine conjugate comprising 500 *E. acervulina* oocysts complexed with either 25 or 150 µl of polyclonal antibody; controls were a non-vaccinated control (cntrl) and a control vaccinated with oocysts but without antibody (0).
Figure 5:
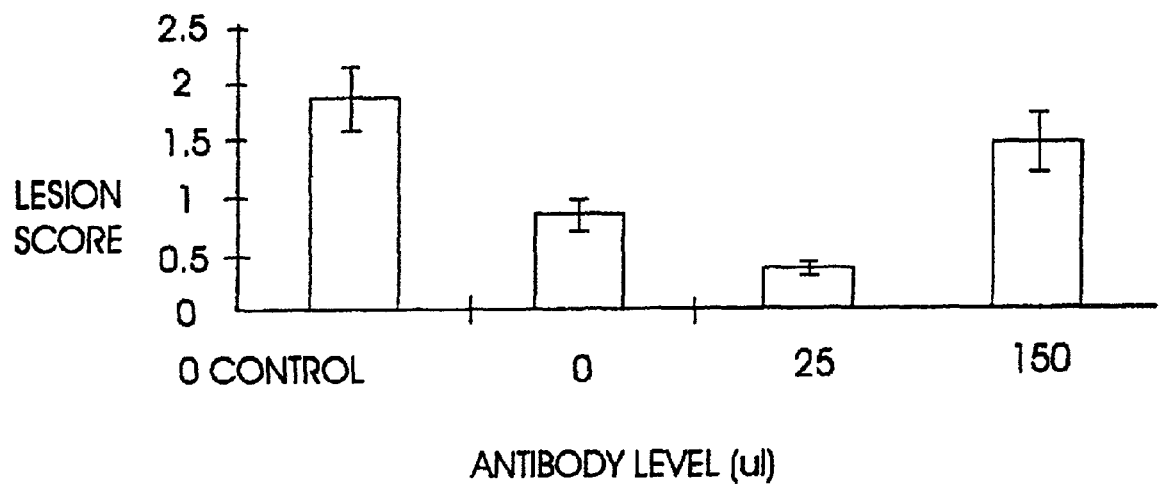
FIG. 5 graphs lesion scores in birds after vaccination and a high-dose *E. acervulina* challenge. Vaccination used a vaccine conjugate comprising 500 *E. acervulina* oocysts complexed with either 25 or 150 µl of polyclonal antibody; controls were a non-vaccinated control (cntrl) and a control vaccinated with oocysts but without antibody (0).

A high dose challenge (500 oocyst challenge) was administered to all the treatment groups and weight gain and lesion scores were examined. Weight gain results (FIG. 4) did not show a difference among the treatment groups, including vaccinated and non-vaccinated controls. Lesion score data (FIG. 5) indicated protection of all vaccinated groups over the non-vaccinated control.

EXAMPLE 8

*Pasteurella multocida*

Production of antiserum to *P. multocida*: Ten SPF chickens were housed in a clean room from hatch; at four weeks of age each bird received (subcutaneous injection in the neck) 0.5 mls of Solvay's "Pabac", a commercial inactivated *P. multocida* oil emulsion vaccine containing serotypes 1, 3 and 4; at eight weeks of age, an additional 0.5 mls was injected subcutaneously into the neck and another 0.5 mls was injected intramuscularly in the right breast. Approximately 20 mls of blood was removed from each bird by cardiac puncture at ten weeks of age. Antiserum was collected from the blood, pooled, and filtered through a 0.45 μm filter. After numerous sterility tests.all produced negative results, the antisera was placed into different sized vials and placed in a −20 degree C. freezer until use.

Isolation and titer determination of the Cu and M9 strains of P. multocida

The Cu and M9 strains of P. multocida were grown from live vaccines, Choleramune Cu and Multimune M respectively, each produced by Biomune. It was determined that these strains of *P. multocida* freeze best at −70 degrees C. in a mixture of 90% culture and 10% glycerol.

EXAMPLE 9

Hatchability of Eggs Inoculated at Day 18 with *P. multocida*

This experiment was designed to determine if different numbers of colony forming units (CFUs) of *P. multocida* strains Cu and M9 affect the hatchability of SPF eggs following in ovo inoculation at day 18 of incubation. Each strain of *P. multocida* was diluted in Phosphate Buffered Saline (PBS) to produce three dilutions: 1000 CFUs per 0.1 ml; 100 CFUs per 0.1 ml; and 10 CFUs per 0.1 ml. At day 18 of incubation, 0.1 mls of each dilution for each strain was inoculated into fourteen SPF eggs. Thirteen eggs were inoculated with 0.1 ml of a mixture of Brain Heart Infusion Broth (BHI), PBS, and Glycerol (vehicle control) and thirteen eggs received no inoculation.

The results in Table 6 show that hatchability of SPF eggs was severely depressed in groups 2 through 7.

TABLE 6

| | Hatchability of SPF Eggs Following Inoculation at Day 18 with *P. multocida* | | | | | | | |
|---|---|---|---|---|---|---|---|---|
| | Group 1 BHI, PBS Glycerol | Group 2 Cu, 1000 CFUs | Group 3 Cu, 100 CFUs | Group 4 Cu, 10 CFUs | Group 5 M9, 1000 CFUs | Group 6 M9 100 CFUs | Group 7 M9, 10 CFUs | Group 8 No Inocu-lation |
| Normal Hatched | 12 | | | 3 | | | 1 | 11 |
| Un-Hatched | 1 | 14 | 14 | 11 | 14 | 14 | 13 | 2 |
| % Hatched | 92 | 0 | 0 | 21 | 0 | 0 | 7 | 85 |

Each inoculated egg was inoculated with 0.1 ml of a culture/PBS mixture containing the appropriate number of CFUs. The dilutions containing 1×10(2) CFUs/ml were titered for each strain and the titers differed somewhat from the target numbers. Group 4 actually contained 10.5 CFUs/egg, Group 3 contained 105 CFUs/egg, and Group 2 contained 1050 CFUs/egg. Group 7 contained 12.5 CFUs/egg, Group 6 contained 125 CFUs/egg, and Group 5 contained 1250 CFUs/egg. Group 1 eggs were inoculated with 0.1 ml of a BHI/PBS/Glycerol mixture.

EXAMPLE 10

Colony Growth of *P. multocida* after Complexing with Chicken Antiserum

One ml of chicken *P. multocida* antiserum (see Example 8) was removed from −20 degrees C. and thawed at room temperature. The serum was serially diluted, 2-fold, in PBS. One half ml of each serum dilution was mixed with 0.5 ml of *P. multocida* Cu strain culture containing 100 CFUs/0.5 ml. This mixture reacted together for one hour at a room temperature. When one hour had elapsed, 0.5 ml of each serum dilution mixture was plated on TSA plates in duplicate and the 200 CFUs/ml *P. multocida* Cu strain stock solution was plated in triplicate. The plates were incubated for 48 hours at 37 degrees C. Colonies were counted after 24 hours and 48 hours of incubation. Results are shown in Tables 7 and 8.

TABLE 7

| Serum Dilution | CFUs/0.5 ml | Avg | 24 Hours CFUs/1.0 ml of mixture | #CFUs ex-pected* | 48 Hours change in CFU count/ 1.0 ml of mixture |
|---|---|---|---|---|---|
| 1:16 | 114 + 96 | = 105 × 2 = | 210 | 152 | no change |
| 1:32 | 72 + 75 | = 73.5 × 2 = | 147 | 152 | no change |
| 1:64 | 92 + 86 | = 89 × 2 = | 178 | 152 | no change |
| 1:128 | 98 + 71 | = 84.5 × 2 = | 169 | 152 | no change |
| 1:256 | 81 + 92 | = 86.5 × 2 = | 173 | 152 | no change |
| 1:512 | 64 + 80 | = 72 × 2 = | 144 | 152 | no change |
| 1:1024 | 63 + 101 | = 82 × 2 = | 164 | 152 | no change |
| 1:2048 | 73 + 73 | = 73 × 2 = | 146 | 152 | no change |
| 1:4096 | 68 + 81 | = 74.5 × 2 = | 149 | 152 | no change |
| 1:8192 | 60 + 61 | = 60.5 × 2 = | 121 | 152 | no change |
| 1:16384 | 42 + 61 | = 51.5 × 2 = | 103 | 152 | +1 colony |
| 1:32768 | 56 + 59 | = 57.5 × 2 = | 115 | 152 | no change |

*This is the number of CFUs expected in 1 ml of mixture, from the Table 8 titer.

TABLE 8

| Titer of the 2 × 10(2) Stock Solution of *P. multocida* Cu Strain | | | |
|---|---|---|---|
| CFU/0.5 ml | Average | | Per 1.0 ml |
| 176 | 152 × 2 | = | 304 |
| 131 | | | |
| 150 | | | |

Stock solution samples in Table 8 were plated after all mixtures were prepared. The solution did not sit for an additional hour. A mixture of 0.5 ml of this stock solution and 0.5 ml of antiserum yields an expected 152 CFUs/ml of mixture.

The results show a decrease in the number of bacterial CFUs from the least dilute antiserum to the most dilute antiserum (Table 7). This may be due to reaction time. The most dilute antiserum reacted longer with the live culture than the least dilute antiserum (20–30 minutes longer). The increased time may have lead to greater numbers of colonies dying off. Repeated vortexing of the stock solution (3–4 CFUs/ml) may have also contributed to the observed decrease in colony count. The next Example investigates this trend further.

EXAMPLE 11

This experiment investigated the reaction between colonies of *P. multocida* Cu strain and the same dilutions of the *P. multocida* antiserum as shown in Table 6. Instead of vortexing the "2×10(2)" stock solution of *P. multocida* Cu strain continually, as in the previous experiment, the solution was gently mixed by pipetting. To form each antibody-bacterium complex, one ml of antiserum dilution was mixed with one ml of stock culture dilution. This mixture was allowed to react for four hours. The stock solution was plated on TSA plates in triplicate and was found to contain 186 CFUs/ml (Table 9). The remainder of this solution was also allowed to remain at room temperature for four hours.

Following the four hour reaction time, 0.5 ml of each antibody-bacterium mixture was mixed and plated in duplicate on TSA. The 186 CFU/ml stock solution was mixed and plated on TSA in triplicate (0.5 ml/plate). Colonies were counted at 24 hours after incubation at 37 degrees C. and again after 96 hours. The results are provided in Tables 9 and 10.

TABLE 9

Titer of the planned 2 × 10(2) CFUs/ml final stock solution of *P. multocida* strain Cu

| Immediately after Adding 1 ml samples to serum | | | After sitting at room temperature for 4 hours | | |
|---|---|---|---|---|---|
| CFU/0.5 ml | Average | Per 1 ml | CFU/0.5 ml | Average | Per 1 ml |
| 93 | 93 | 186 | 39<br>47<br>48 | 44.7 | 89 |

TABLE 10

| Serum Dilution | 24 Hours CFUs/0.5 ml | Avg | CFUs/1.0 ml | #CFUs expected* | 96 Hours |
|---|---|---|---|---|---|
| 1:16 | 114 + 92 | 103 | 206 | 93 | no change |
| 1:32 | 79 + 73 | 76 | 152 | 93 | no change |
| 1:64 | 50 + 48 | 49 | 98 | 93 | no change |
| 1:128 | 58 + 69 | 63.5 | 127 | 93 | no change |
| 1:256 | 52 + 67 | 59.5 | 119 | 93 | no change |
| 1:512 | 72 + 63 | 67.5 | 135 | 93 | no change |
| 1:1024 | 55 + 63 | 59 | 118 | 93 | no change |
| 1:2048 | 55 + 62 | 58.5 | 117 | 93 | no change |
| 1:4096 | 51 + 53 | 52 | 104 | 93 | no change |
| 1:8192 | 28 + 34 | 31 | 64 | 93 | no change |
| 1:16384 | 20 + 26 | 23 | 46 | 93 | no change |
| 1:32768 | 24 + 20 | 22 | 44 | 93 | no change |

The data in Table 10 shows the same decreasing colony count with increasing antiserum dilution as was seen in the previous experiment, slightly more pronounced. There appears to be more CFUs/ml than expected in dilution mixtures 1:16 through 1:4096. Similar findings were also presented in Table 7. The colony counts found in Table 9 suggest the CFUs die off in PBS over time in the absence of serum. This may account for the lower than expected colony counts in dilutions 1:8192 through 1:32768 in both studies. The antiserum may be demonstrating some growth inhibiting capabilities at the higher dilutions while exhibiting growth enhancement effects in the least dilute mixtures. The next experiment was conducted to investigate possible causes of these observations.

EXAMPLE 12

The effects of *P. multocida* antiserum and negative serum (chicken serum containing no *P. multocida* antibodies) on the growth of the M9 strain of *P. multocida* was compared in vitro. Serum dilutions and *P. multocida* culture dilutions were prepared as in Example 11. One ml of culture containing 139 CFUs per ml (Table 6) was mixed with one ml of dilute serum. Three dilutions (1:16, 1:512, and 1:32768) of negative serum were prepared and mixed with the appropriate amount of bacterial culture. The bacterial culture/serum dilution mixtures reacted together for one hour at room temperature.

The serum antibody-bacterium mixtures were plated on TSA plates (0.5 ml) in duplicate and the negative serum bacterium mixtures were plated in triplicate following the one hour reaction time. The *P. multocida* strain M9 stock solution was plated in triplicate after adding 1.0 ml to all antiserum and negative serum dilutions and again after allowing it to remain at room temperature for one hour. Colonies were counted after incubating for 24 hours at 37 degrees C. and any changes in counts were noted after 48 hours of incubation. The results of these counts are given in Tables 11 and 12.

TABLE 11

Titer of the planned 2 × 10(2) CFU/ml final stock solution of *P. multocida* M9

| Immediately after adding 1 ml samples to serum | | | After sitting at room temperature for 1 hour | | |
|---|---|---|---|---|---|
| CFU/0.5 ml | Average | Per 1 ml | CFU/0.5 ml | Average | Per 1 ml |
| 68<br>76<br>64 | 69.3 | 138.6 | 61<br>63<br>69 | 64.3 | 128.6 |

TABLE 12

| Serum Dilution | *P. multocida* antiserum after 24 hrs CFUs/ 0.5 ml | Avg. | Per 1 ml | # CFUs expected in 1 ml* | Negative antiserum after 24 hours CFUs/ 0.5 ml | Avg. | Per 1 ml |
|---|---|---|---|---|---|---|---|
| 1:16 | 36 + 34 | 35 | 70 | 69 | 34 + 55 + 50 | 46.3 | 92.6 |
| 1:32 | 39 + 33 | 36 | 72 | 69 | | | |
| 1:64 | 40 + 37 | 38.5 | 77 | 69 | | | |
| 1:128 | 53 + 33 | 43 | 86 | 69 | | | |
| 1:256 | 33 + 35 | 34 | 68 | 69 | | | |
| 1:512 | 34 + 51 | 42.5 | 85 | 69 | 44 + 43 + 40 | 42.3 | 84.6 |
| 1:1024 | 36 + 35 | 35.5 | 71 | 69 | | | |
| 1:2048 | 32 + 37 | 34.5 | 69 | 69 | | | |
| 1:4096 | 34 + 29 | 31.5 | 63 | 69 | | | |
| 1:8192 | 34 + 44 | 39 | 78 | 69 | | | |
| 1:16384 | 24 + 25 | 24.5 | 49 | 69 | | | |
| 1:32768 | 18 + 38 | 28 | 56 | 69 | 40 + 39 + 33 | 37.3 | 74.6 |

*Number of CFUs expected in 1 ml of mixture from Table 11 titer.

There were no changes in the colony counts after 48 hours of incubation at 37 degrees C.

The data in Examples 10–12 show initial increases leading to gradual decreases in the number of CFUs as antiserum to *P. multocida* became more dilute. The combined data suggest that both strains of *P. multocida* may actually use the serum as a growth medium. As the serum concentration decreases so does the growth of *P. multocida*. Some of the results suggest that *P. multocida* dies off when diluted in PBS and sits at room temperature for between one and four hours. This may account for the fewer than expected CFUs observed from the 1:8192 dilutions through 1:32768 dilutions. As the serum becomes less concentrated, the PBS concentration increases. There was not a large difference, though, in the stock colony counts in the present example, before and after a one hour waiting period, yet the low counts in the higher dilutions still existed.

The colony counts for the serum mixtures containing no antibodies to *P. multocida*, when compared to their *P. multocida* antibody-containing counterparts and stock counts, may be showing some growth inhibition capabilities of the antiserum with *P. multocida* antibodies. CFU counts in the samples without *P. multocida* antiserum started high and decreased but not to a level lower than expected when compared to the stock CFU counts after one hour. CFU counts were lower in two of three samples containing antibodies to *P. multocida* than in the negative serum samples without *P. multocida* antibodies. A growth inhibiting of *P. multocida* antiserum may be masked by other factors present.

EXAMPLE 13

Hatchability of Eggs Injected at Day 18 of Incubation with *P. multocida* antiserum-*P.multocida* CFUs This study was designed to test the effect of serum antibody-bacterium complexes when administered in ovo to SPF eggs. The same number of CFUs (five were targeted) of *P. multocida* strain M9 was mixed with varying amounts of *P. multocida* antiserum and then 0.1 ml of each mixture was inoculated into fifteen SPF eggs in each of seven groups. A 100 CFUs/ml stock solution was prepared using *P. multocida* strain M9 culture. To insure that each egg received the same number of CFUs, the appropriate amount of serum was mixed with the appropriate amount of the stock solution for each group at five minute intervals. These mixtures remained room temperature for thirty minutes, after which time, 0.1 ml was inoculated into fifteen eggs at day eighteen of incubation. The 100 CFUs/ml stock solution was plated in triplicate following the preparation of the final group's mixture and again after the final group's mixture reacted for 30 minutes (Table 13). The plates were all incubated at 37 degrees C. for 24 hours, after which, colonies were counted. Table 14 provides hatchability data for each group.

TABLE 13

Titer of the planned 1 × 10(2) *P. multocida* Strain M9 Stock Solution

|  | CFUs/0.5 ml | Average | Per 1 ml |
|---|---|---|---|
| Pre-30 minutes | 38 | 32 | 64 |
|  | 28 |  |  |
|  | 30 |  |  |
| Post-30 minutes | 30 | 29 | 58 |
|  | 30 |  |  |
|  | 27 |  |  |

TABLE 14

Hatchability effects of inoculating SPF eggs at day 18 of incubation with 1 ml of mixtures containing antiserum to *P. multocida* and CFUs of the M9 strain of *P. multocida*.

|  | Group 1 no serum +3.2 CFUs | Group 2 0.1 µl serum +3.2 CFUs | Group 3 1.0 µl serum +3.2 CFUs | Group 4 10.0 µl serum +3.2 CFUs | Group 5 25.0 µl serum +3.2 CFUs | Group 6 50.0 µl serum +3.2 CFUs | Group 7 50.0 µl serum 50.0 µl PBS egg |
|---|---|---|---|---|---|---|---|
| Normal Hatched |  | 2 | 1 |  | 2 | 4 | 15 |
| Hatched (Dead) |  |  |  |  |  |  |  |
| Hatched (clinically affected) | 1 |  | 3 | 3 | 3 | 5 |  |
| Un-hatched | 14 | 13 | 11 | 12 | 10 | 6 |  |
| % hatched | 6.7 | 13.3 | 26.7 | 20.0 | 33 | 60.0 | 100 |

This study was originally designed to inoculate each egg that was to receive bacteria with 5.0 CFUs mixed with the appropriate volume of *P. multocida* antiserum. The titer information found in Table 13 shows that the eggs received a number of CFUs closer to 3.2 than to 5 and that little colony loss occurred as a result of the 30 minute reaction period. The results in Table 14 show that even small numbers of CFUs of *P. multocida* strain M9 are devastating to SPF eggs when administered at day eighteen of incubation. The controls in group 7 experienced a 100% hatch. The hatch was severely affected in the other groups. Of these groups, 5 and 6 contained the next highest percentages of total hatched birds. The eggs in group 6 were inoculated with the highest ratio of antiserum to *P. multocida* (50 µl+3.2 CFUs) and experienced a 60% overall hatch with a 27% normal hatch. This trend suggests that antiserum to *P. multocida*, when combined with the live bacteria, may provide some degree of protection to a chicken embryo by either decreasing or delaying the pathogenic effects of the bacterium.

The data in Tables 12 and 14, comparing serum with and without *P. multocida* antibodies and different amounts of serum antibodies respectively, show a possible inhibitory effect of serum antibodies to *P. multocida* on the growth, and perhaps the pathogenic effects, of the organism. In Table 14 it was shown that the two highest amounts of antibody (Groups 5 and 6) resulted in better hatches compared to the bacterium alone (Group 1).

EXAMPLE 14

Growth of *M. gallisepticum*; Production of Hyperimmune Sera

A culture of the bacterium *Mycoplasma gallisepticum* strain F was obtained from North Carolina State University, Mycoplasma Lab, College of Veterinary Medicine. The F strain of M. gallisepticum is used in the commercial layer industry as a live vaccine. Forty milliliters of Frey's Media supplemented with 15% swine serum (FMS) was inoculated with 1.33 mls of the bacterial culture. This mixture was then incubated for approximately 18 hours at 37 degrees C. and the grown culture was mixed 80/20 with sterile glycerol for freezing at −70degrees C. Sterility of this mixture was tested on Trypticase Soy Agar (TSA) and no extraneous organisms grew. Titer determination for the M. gallisepticum strain F stock culture after 24 hours at −70degrees C. was $5.8 \times 10(8)$ CFUs/ml.

Antiserum to M. gallisepticum strain R was purchased from the NCSU Mycoplasma Lab. The antiserum was produced by hyperimmunizing New Zealand White rabbits with inactivated M. gallisepticum strain R in adjuvant. Rabbits were immunized by intramuscular and intradermal injections three times prior to blood collection. This antiserum is designated as MGA.

EXAMPLE 15

Growth Inhibition Effect of MGA on M. gallisepticum Strain F

This experiment investigated the growth of a given amount of M. gallisepticum strain F over time after the organism was mixed with different amounts of MGA. A sample of MGA was initially diluted 1:10 in phosphate buffered saline (PBS). Then, the antiserum was further diluted by making 10 serial 1:2 dilutions by adding 0.5 ml of the previous dilution to 0.5 ml of PBS (dilutions 1:20 through 1:10240). One vial of M. gallisepticum F stock culture was thawed at room temperature and diluted 1:100. This $10(-2)$ stock solution contained $5.8 \times 10(6)$ CFUs/ml. Bacterium-antibody complexes were prepared by adding 0.4 ml of the $5.8 \times 10(6)$ stock solution to 0.4 ml of each of the 11 MGA dilutions. These complexes were allowed to react at room temperature for 30 minutes. Treatment 12 consisted of 0.4 ml PBS added to 0.4 ml of the same bacterial stock solution.

Following the 30 minute reaction time, each of the 12 treatments was serially diluted in FMS from $10(-1)$ through $10(-8)$. These tubes were incubated for 14 days and growth was determined at 41 hours, 47.5 hours, and at 14 days. (Growth of M gallisepticum is detected in FMS by a color change. As bacterial growth increases the pH of the medium decreases, causing a color change in the pH indicator phenol red. As growth occurs the color gradually changes from a deep red to orange and eventually to yellow. The degree of growth can be scored based on the medium color). Results are provided in Table 15.

TABLE 15

Growth of MgF after 0.4 ml of 12 antiserum dilutions, containing between .039 µl and 40.0 µl antiserum, were mixed with 0.4 ml of an MgF stock solution

| Treatment | MgF* | .4 ml MgF** | Growth after 41 Hours | | | | | Growth after 47.5 Hours | | | | | MgF Presence*** |
|---|---|---|---|---|---|---|---|---|---|---|---|---|---|
| | | | 10(−1) | 10(−2) | 10(−3) | 10(−4) | 10(−5) | 10(−1) | 10(−2) | 10(−3) | 10(−4) | 10(−5) | |
| 1 | 40 µl | .4 ml | − | − | − | − | − | − | +/− | − | − | − | 10(−7) |
| 2 | 20 µl | .4 ml | − | +/− | − | − | − | − | ++ | + | − | − | 10(−6) |
| 3 | 10 µl | .4 ml | +/− | +/− | +/− | − | − | − | +++ | + | − | − | 10(−6) |
| 4 | 5 µl | .4 ml | ++ | +/− | − | − | − | ++++ | +++ | + | − | − | 10(−7) |
| 5 | 2.5 µl | .4 ml | ++++ | +/− | − | − | − | ++++ | +++ | +/− | − | − | 10(−6) |
| 6 | 1.25 µl | .4 ml | ++++ | +/− | − | − | − | ++++ | +++ | +/− | − | − | 10(−6) |
| 7 | .625 µl | .4 ml | ++++ | +/− | +/− | +/− | − | ++++ | +++ | − | − | − | 10(−6) |
| 8 | .313 µl | .4 ml | ++++ | + | +/− | +/− | +/− | ++++ | +++ | + | +/− | +/− | 10(−6) |
| 9 | .156 µl | .4 ml | ++++ | +/− | +/− | − | − | ++++ | +++ | +/− | − | − | 10(−7) |
| 10 | .078 µl | .4 ml | ++++ | +/− | +/− | − | − | ++++ | ++ | +/− | − | − | 10(−7) |
| 11 | .039 µl | .4 ml | ++++ | +/− | +/− | − | − | ++++ | ++ | +/− | − | − | 10(−6) |
| 12 | | .4 ml | ++++ | +/− | − | − | − | ++++ | ++ | − | − | − | 10(−7) |

MgF* = MgF antiserum in .4 ml
.4 ml MgF** = .4 ml MgF 2.32 × 10(−6)
MgF Presence*** = Presence of MgF through dilution tube (after 14 days of incubation)
− (no growth; deep red)
+/− (growth just beginning; lighter red color than control tubes)
+ (light growth; light red)
++ (moderate growth; deep orange)
+++ (moderate to heavy growth; light orange)
++++ (heavy growth; yellow)

Growth was detected in all 12 treatments by day 14 (Table 1). Growth was delayed in Groups 1–4, the groups containing the highest levels of MGA. Growth in these groups was not evident as early as in the groups with lower levels of MGA. These findings suggest that the higher levels of MGA had a growth inhibiting effect on the bacterium.

EXAMPLE 16

Growth Inhibition Effects of MGA on *M. gallisepticum*

A vial of *M. gallisepticum* strain F stock was thawed and diluted 1:100 in FMS. This 10(−2) dilution contained approximately 5×10(6) CFUs/ml. One ml of the 10(−2) stock dilution was placed into each of eight dilution tubes after being thoroughly mixed. A certain amount of MGA was added to each tube (see Table 16) and the bacterium/antiserum complexes were mixed. They were incubated at room temperature for 15 minutes and then at 37degrees C. Growth was determined over the course of 13 days using color change in the FMS growth medium as an indicator. Results are given in Table 16.

TABLE 16

| MgF 5.0 × 10(6) CFU/ml | μls of Mg Antiserum (MGA) | Growth after 27 hours at 37° C. | Growth after 46 hours at 37° C. | Growth after 13 days at 37° C. |
|---|---|---|---|---|
| 1.0 ml | No serum | +++ | ++++ | ++++ |
| 1.0 ml | 48 | no growth | no growth | ++++ |
| 1.0 ml | 24 | no growth | no growth | ++++ |
| 1.0 ml | 12 | no growth | no growth | ++++ |
| 1.0 ml | 6 | no growth | + | ++++ |
| 1.0 ml | 3 | no growth | ++ | ++++ |
| 1.0 ml | 1.5 | no growth | +++ | ++++ |
| 1.0 ml | 0.5 | ++ | ++++ | ++++ |

+ (light growth; light red)
++ (moderate growth; deep orange)
+++ (moderate to heavy growth; light orange)
++++ (heavy growth; yellow)

Moderate growth of *M. gallisepticum* occurred within the first 27 hours of incubation in the tube that did not contain antiserum and growth was heavy in this tube by 46 hours at 37 degrees C. (Table 16). Bacterial growth was not detected within the first 27 hours of incubation in the tubes that contained greater than or equal to 1.5 μls MGA. After 46 hours of incubation, growth was still not detected in the tubes that contained 12, 24, and 48 μls of MGA. All tubes showed heavy growth of *M. gallisepticum* after 13 days at 37 degrees C. These results show that the bacterium was present in all tubes, but that higher amounts of antiserum delayed growth for longer periods of time than did lesser amounts. The time that it took for growth to be detected appears to be directly proportional to the amount of MGA in the bacterium-antiserum complex.

EXAMPLE 17

Effect of *M. gallisepticum*-MGA Complexes on Hatch

Nine groups of eggs were inoculated at day 18 of incubation. Seven of the groups were inoculated with one of seven different *M. gallisepticum* strain F-MGA complexes. One group was inoculated with the bacterium only and another group was inoculated with a 1:4 dilution of FMS in PBS.

A vial of *M. gallisepticum* strain F stock was thawed and diluted 1:5 and 1:10 in 10% FMS and 90% PBS diluent. Appropriate amounts of these dilutions were used to create the bacterium-MGA complexes. Each egg received a 0.1 ml injection containing the same number of *M. gallisepticum* CFUs with the appropriate amount of antiserum for a particular group, except for Group 1. The eggs in Group 1 received 0.1 ml of the FMS/PBS diluent. The complexes were allowed to react together for 10 minutes before inoculation. The eggs were then incubated until hatch.

The 1:10 dilution of the bacterial stock was titered by making 3 serial dilution series through 10(−9) and plating the 10(−6) dilutions of two dilution series TSA and incubating at 37° C. All tubes in all three serial dilution series showed *M. gallisepticum* growth. The titer was 8×10(8) CFUs/ml. Hatchability results are provided in Table 17.

TABLE 17

| Group | MgF CFUs | Amount of Mg Antiserum (MGA) | # Eggs Hatched/ # Eggs Injected | # Healthy Chicks/ # Eggs Injected |
|---|---|---|---|---|
| 1 | 0 | 0 | 13/14 (93%) | 12/14 (86%) |
| 2 | 8.0 × 10(6) | 40 μl | 10/11 (91%) | 8/11 (73%) |
| 3 | 8.0 × 10(6) | 20 μl | 10/10 (100%) | 8/10 (80%) |
| 4 | 8.0 × 10(6) | 10 μl | 6/11 (55%) | 0/11 (0%) |
| 5 | 8.0 × 10(6) | 5 μl | 10/10 (100%) | 2/10 (20%) |
| 6 | 8.0 × 10(6) | 2 μl | 6/11 (55%) | 1/11 (9%) |
| 7 | 8.0 × 10(6) | 0.5 μl | 7/11 (64%) | 0/11 (0%) |
| 8 | 8.0 × 10(6) | .05 μl | 8/11 (73%) | 0/11 (0%) |
| 9 | 8.0 × 10(6) | 0 | 8/14 (57%) | 0/14 (0%) |

The MGA-*M. gallisepticum* complexes influenced the percent hatch and chick health. The groups that experienced hatches above 90% were the groups that contained the largest proportions of MGA to CFUs (with the exception of Group 4). The percentage of health chicks was much higher in Groups 2 and 3 than in other groups receiving MGA-bacterium complexes with less antiserum in the formulation. These findings indicate that certain MGA:bacterium ratios have the capability of protecting a developing chicken embryo by delaying and/or decreasing the pathogenic effects of the bacterium.

EXAMPLE 18

M. gallisepticum strain F/Antibody Complex Vaccine

Six groups of 16 viable eggs were inoculated at day 18 of incubation. The 16 eggs in the negative control group (Group 6) were inoculated on day 18 with 0.1 ml of diluent (1 part FMS in 9 parts PBS), and hatched in a large hatcher unit that contained no other eggs.

A vial of M. gallisepticum strain F stock was thawed at room temperature and diluted 1:5 (stock 2). The titration of stock 2 showed that it contained 7×10(7) CFUs/ml. Stock 2 was then divided into 0.9 ml aliquots and combined with 0,5,10,20 or 40 μl of MGA. Once mixed, the bacterium-MGA formulations were allowed to incubate at room temperature for 15 minutes. These bacterium-MGA complexes were administered to eggs of each group in 0.1 ml doses. Group 1 eggs received inoculations containing only bacteria. Each group of 16 eggs was then placed in separate small hatcher units until day of hatch. The MGA-M. gallisepticum formulations tested CFUs are shown in Table 18.

The remaining stock 2 dilution was titrated in three separate serial 10-fold dilutions to 10(−9) using FMS. The 10(−4), 10(−5) and 10(−6) dilution tubes in each series was plated in quadruplicate on FMS agar and incubated at 37° C. for 9 days.

On the day of hatch, Groups 1–5 were processed. Normal, healthy looking chicks were sampled for the presence of M. gallisepticum by swabbing the choanal cleft with a sterile swab and inoculating tubes containing 1.8 mls of FMS. After the chicks were processed, the sampled chicks from each group were placed in a P2 containment room. Each group was placed in a separate brooder cage and no two cages were in contact.

The chicks in vehicle control Group 6 experienced a delayed hatch and were processed the day following the hatch of groups 1–5. Ten control birds were swabbed for the presence of M. gallisepticum and were placed in a brooder cage in a separate P2 containment room. On 21 days of age, all surviving chicks were bled and serum collected for determination of antibodies to M. gallisepticum by serum plate agglutination (SPA) and ELISA. Results are provided in Table 18.

TABLE 18

| Group | 1* | 2 | 3 | 4 | 5 | 6 |
|---|---|---|---|---|---|---|
| #CFUs/egg | 1.4 × 10(6) | 3.5 × 10(6) | 3.5 × 10(6) | 3.5 × 10(6) | 3.5 × 10(6) | no CFUs |
| MGA/egg | 0 μl | 5 μl | 10 μl | 20 μl | 40 μl | 100 μl diluen |
| # Normal Hatched | 0 | 0 | 0 | 8 | 12 | 10 |
| # Clinically Affected Hatched | 9 | 7 | 8 | 3 | 2 | 1 |
| Unhatched/Dead | 7 | 9 | 8 | 5 | 2 | 5 |
| % Hatched | 56.25 | 43.75 | 50.0 | 68.75 | 87.5 | 68.75 |
| % Normal Hatched | 0 | 0 | 0 | 50 | 75 | 62.5 |
| # Chicks Placed | 0 | 0 | 3 | 9 | 10 | 10 |
| # Chicks Alive at 3 weeks | NA | NA | 1 | 2 | 7 | 10 |
| MgF Reisolation # Positive/# Sampled | Not Tested | 3/3 | 3/3 | 9/9 | 9/10 | 0/10 |
| SPA** # Positive/# Sampled | NA | NA | 1/1 | 2/2 | 6/7 | 0/10 |
| Mean ELISA Titer | NA | NA | 599 | 643 | 645 | 0 |

*Due to a calculation error, the eggs in Group 1 received 1.4 × 10(6) CFUs.
**All positive SPA reactions were scored a 3 or higher on a scale of 0–4, with 4 being the strongest reaction.

The eggs receiving the bacterium without antiserum (Group 1) and the two lower amounts of MGA plus M. gallisepticum (Groups 2 and 3) had the lowest percent hatches and no normal birds hatched. The vehicle control group (Group 6) experienced a delayed hatch as well as a poorer hatch than expected. This probably was caused by the fact that the eggs were incubated in a large hatcher intended for the incubation of 2000 eggs. Despite this hatch problem, 10 chicks were healthy and they tested negative for M gallisepticum isolation and the two serum antibody tests. Groups 4 and 5 experienced percent hatches and percent normal hatches that showed great improvement over those of Groups 1, 2 and 3. The eggs in these two groups received higher levels of MGA and Group 5 (3.5×10(6)CFU+40 μl MGA) experienced the best hatch of all the groups. All birds remaining alive at the time of serum collection were healthy.

The antibody response to *M. gallisepticum* measured by the SPA test and ELISA indicate that the *M. gallisepticum* strain F complex vaccines were efficacious for birds in Groups 3, 4 and 5.

It is interesting to note that one bird in Group 5 was negative for *M. gallisepticum* reisolation at hatch, the SPA test, and ELISA. All the other birds that were sampled from Groups 3,4 and 5 tested positive in each case. It appears that one bird in Group 5 never became infected.

Examples 14–18 were designed to test the usefulness of a bacteria:antibody vaccine complex. The data support the concept that addition of specific antiserum (specific for the vaccine bacteria) to live bacteria in the appropriate ratio provides protection to the chick embryo by decreasing or delaying the pathogenic effects of the bacterium while at the same time allowing an efficacious immune response to develop in the hatchlings, as evidenced by an active humoral immune response.

That which is claimed is:

1. A method of improving the safety of a live protozoa vaccine that produces protective immunity against a protozoal disease in a subject, said method comprising:

administering to the subject a vaccine conjugate comprising a live pathogenic protozoa and a neutralizing factor bound to the live protozoa, the neutralizing factor selected from the group consisting of neutralizing antibodies and neutralizing antibody fragments which are capable of neutralizing the live protozoa;

wherein the neutralizing factor is provided in the vaccine conjugate in an amount that temporarily neutralizes the live protozoa, so that the pathogenic effects of the live protozoa in the vaccine are delayed due to the addition of the neutralizing factor as compared with the pathogenic effects of the live protozoa in the absence of the neutralizing factor, and the live protozoa retains the ability to replicate and infect the subject and induce a protective immune response against a later challenge with the live protozoa in the subject.

2. The method according to claim 1, wherein the live protozoa is capable of causing disease in the subject.

3. The method according to claim 1, wherein the neutralizing factor is selected from the group consisting of IgG immunoglobulins and IgG immunoglobulin fragments.

4. The method according to claim 1, wherein the live protozoa is a live *Elmeria*.

5. The method according to claim 4, wherein the live protozoa comprises a protozoa selected from the group consisting of a live *E. tenella, E. acervulina, E. necatrix, E. brunetti, E. mivati, E. maxima* and combinations thereof.

6. The method according to claim 1, wherein the subject is a mammalian subject.

7. The method according to claim 1, wherein the subject is an avian subject.

8. The method according to claim 1, wherein the neutralizing factor is of polyclonal origin.

9. The method according to claim 1, wherein the neutralizing factor is of monoclonal origin.

10. The method according to claim 1, wherein the subject is administered the vaccine conjugate by a method selected from the group consisting of subcutaneous administration, intraperitoneal administration, and intramuscular administration.

11. An improved vaccine preparation for more safely producing protective immunity against a protozoal disease in a subject, said vaccine preparation comprising:

a pharmaceutically acceptable formulation comprising a vaccine conjugate comprising a live pathogenic protozoa and a neutralizing factor bound to said live protozoa, said neutralizing factor selected from the group consisting of neutralizing antibodies and neutralizing antibody fragments which are capable of neutralizing the live protozoa;

wherein said neutralizing factor is provided in said vaccine conjugate in an amount that temporarily neutralizes said live protozoa, so that the pathogenic effects of said live protozoa in the vaccine preparation are delayed due to the addition of the neutralizing factor as compared with the pathogenic effects of the live protozoa in the absence of said neutralizing factor, and said live protozoa retains the ability to replicate and infect a subject and induce a protective immune response against a later challenge with the live protozoa in said subject.

12. The vaccine preparation according to claim 11, wherein said live protozoa is capable of causing disease in said subject.

13. The vaccine preparation according to claim 12, wherein said live protozoa is capable of causing disease in an avian subject.

14. The vaccine preparation according to claim 12, wherein said live protozoa is capable of causing disease in a mammalian subject.

15. The vaccine preparation according to claim 11, wherein said pharmaceutically acceptable formulation is lyophilized.

16. The vaccine preparation according to claim 11, wherein said pharmaceutically acceptable formulation is a liquid.

17. The vaccine preparation according to claim 11, wherein said live protozoa is a live *Eimeria*.

18. The vaccine preparation according to claim 11, wherein said live protozoa comprises a protozoa selected group consisting of a live *E. tenella, E. acervulina, E. necatrix, E. brunetti, E. mivati, E. maxima* and combinations thereof.

19. A method of improving the safety of a live protozoa vaccine that produces protective immunity against a protozoal disease in an avian subject, said method comprising:

administering to the avian subject in ovo a vaccine conjugate comprising a live pathogenic protozoa and a neutralizing factor bound to the live protozoa, the neutralizing factor selected from the group consisting of neutralizing antibodies and neutralizing antibody fragments which are capable of neutralizing the live protozoa;

wherein the neutralizing factor is provided in the vaccine conjugate in an amount that temporarily neutralizes the live protozoa, so that the pathogenic effects of the live protozoa in the vaccine are delayed due to the addition of the neutralizing factor as compared with the pathogenic effects of the live protozoa in the absence of the neutralizing factor, and the live protozoa retains the ability to replicate and infect the avian subject and induce a protective immune response against a later challenge with the live protozoa in the avian subject.

20. The method according to claim 19, wherein the live protozoa is capable of causing disease in the avian subject.

21. The method according to claim 19, wherein the neutralizing factor is selected from the group consisting of IgG immunoglobulins and IgG immunoglobulin fragments.

22. The method according to claim 19, wherein the neutralizing factor is of polyclonal origin.

23. The method according to claim 19, wherein the neutralizing factor is of monoclonal origin.

24. The method according to claim 19, wherein the live protozoa is a live *Eimeria*.

25. The method according to claim 24, wherein the live protozoa comprises a protozoa selected from the group consisting of a live *E. tenella, E. acervulina, E. necatrix, E. brunetti, E. mivati, E. maxima* and combinations thereof.

26. The method according to claim 19, wherein the avian subject is selected from the group consisting of a chicken, a turkey, a duck, a goose, a quail and a pheasant.

27. The method according to claim 26, wherein the avian subject is a turkey.

28. The method according to claim 26, wherein the avian subject is a chicken.

29. The method according to claim 19, wherein the vaccine conjugate is administered to the avian subject during the fourth quarter of in ovo incubation.

30. The method according to claim 28, wherein the vaccine conjugate is administered to the avian subject at about day fifteen to about day nineteen of in ovo incubation.

31. The method according to claim 30, wherein the vaccine conjugate is administered to the avian subject at about day eighteen of in ovo incubation.

32. The method according to claim 19, wherein the vaccine conjugate is administered to a region of the egg selected from the group consisting of the amniotic region, the yolk sac, and the air cell.

33. The method according to claim 32, wherein the vaccine conjugate is administered to the amniotic region of the egg.

* * * * *

UNITED STATES PATENT AND TRADEMARK OFFICE
CERTIFICATE OF CORRECTION

PATENT NO. : 6,890,527 B2
DATED : May 10, 2005
INVENTOR(S) : Thoma et al.

It is certified that error appears in the above-identified patent and that said Letters Patent is hereby corrected as shown below:

Column 25,
Line 47, should read -- protozoa is a live *Eimeria*. --;

Column 26,
Line 38, should read -- wherein said live protozoa comprises a protozoa selected from the --.

Signed and Sealed this

Sixth Day of September, 2005

JON W. DUDAS
*Director of the United States Patent and Trademark Office*